United States Patent [19]
Sokalski et al.

[11] Patent Number: 6,126,801
[45] Date of Patent: Oct. 3, 2000

[54] LOW DETECTION LIMIT ION SELECTIVE MEMBRANE ELECTRODES

[75] Inventors: Tomasz Sokalski, Warsaw, Poland; Ernö Pretsch, Uetikon am See, Switzerland

[73] Assignee: Orion Research, Inc., Beverly, Mass.

[21] Appl. No.: 09/121,383

[22] Filed: Jul. 23, 1998

Related U.S. Application Data

[60] Provisional application No. 60/053,665, Jul. 24, 1997, and provisional application No. 60/057,287, Aug. 29, 1997.

[51] Int. Cl.[7] .................................................. G01N 27/26
[52] U.S. Cl. .......................................... 204/418; 204/416
[58] Field of Search ................................... 204/403, 416, 204/418; 205/789, 792, 793

[56] References Cited

U.S. PATENT DOCUMENTS

| | | | |
|---|---|---|---|
| 3,103,480 | 9/1963 | Watanabe et al. | 204/420 |
| 4,981,571 | 1/1991 | Panoch et al. | 204/418 |
| 5,395,505 | 3/1995 | Band et al. | 204/418 |
| 5,419,826 | 5/1995 | Zirino | 204/416 |
| 5,472,590 | 12/1995 | Yamashita et al. | 204/418 |

OTHER PUBLICATIONS

CAPLUS abstract of Quagraine et al. ("Copper(II)–ion selective electrodes based on .alpha.alpha.'–dipyridyl, oxine and cupferron" Ghana J. Chem. (1994), 1(9), 409–19.

Eric Bakker et al., "Detection limit of ion–selective bulk optodes and corresponding electrodes", *Analytica Chimica Acta*, 282 (1993), pp. 265–271.

Urs Schefer et al., "Neutral Carrier Based $Ca^{2+}$ Selective Electrode with Detection Limit in the Sub–Nanomolar Range", *Anal. Chem.*, 1986, 58, pp. 2282–2285.

W.E. Morf, *The Principles of Ion–Selective Electrodes and of Membrane Transport*, Elsevier, New York, 1981, pp. 171–183.

Sokalski et al., "Determination of True Selectivity Coefficients of Neutral Carrier Calcium Selective Electrode", *Mikrochim. Acta*, 1991, I, pp. 285–291.

Bakker et al., "Selectivity of Polymer Membrane–Based Ion–Selective Electrodes: Self–Consistent Model Describing the Potentiometric Response in Mixed Ion Solutions of Different Charge", *Anal. Chem.*, 1994, 66, pp. 3021–3030.

Eric Bakker, "Determination of Unbiased Selectivity Coefficients of Neutral Carrier–Based Cation–Selective Electrodes", *Anal. Chem.*, 1997, 69, pp. 1061–1069.

Guilbault et al., "Recommendations for Nomenclature of Ion–Selective Electrodes", *Pure Appl. Chem*, vol. 48, pp. 127–132.

*Primary Examiner*—Jill Warden
*Assistant Examiner*—Alex Noguerola
*Attorney, Agent, or Firm*—Ernest V. Linek; Banner & Witcoff, Ltd.

[57] ABSTRACT

A new type of ion-selective solvent polymeric or liquid membrane electrode is constructed which allows to extend the measuring range at the lower end by at least six (6) orders of magnitudes. The new method can be used with membranes based on a neutral ionophore, a charged ionophore, or an ion-exchanger. Low detection limits are achieved by maintaining a very low and constant concentration of the primary ion and a sufficiently high concentration of an interfering ion in the internal reference solution. The low and constant concentration of the primary ion is either adjusted with the help of a solution of a hydrophilic ion buffer such as ethylenediamine tetraacetic acid or by adding an excess of a salt of an ion which forms a sparingly soluble salt with the primary ion, such as NaI for the primary ion $Ag^+$. With the new technique, ion-selective electrodes can be used, for the first time, for environmental monitoring of heavy metal ions such as $Pb^{2+}$ and $Cd^{2+}$ at the submicromolar level.

11 Claims, 5 Drawing Sheets

LOW DETECTION LIMIT ION SELECTIVE MEMBRANE ELECTRODES

CROSS-REFERENCE TO RELATED APPLICATIONS

This application claims benefit of the following copending provisional applications; Application No. 60/053,665, filed Jul. 24, 1997 and Application No. 60/057,287, filed Aug. 29, 1997, the disclosures of which are hereby incorporated herein by reference.

BACKGROUND OF THE INVENTION

A large number of ion-selective solvent polymeric or liquid membrane electrodes have been developed during the last decades. A comprehensive list of such electrodes described up to 1990 can be found in Umezawa, *Handbook of Ion-Selective Electrodes: Selectivity Coefficients*; CRC Press: Boca Raton, Ann Arbor, Boston, 1990. Such potentiometric sensors are widely used in clinical analyzers.

The basis of the response is a selective recognition of the target ion, e.g., by selective complexing by a lipophilic ligand, also called an ionophore. In its uncomplexed form, the ionophore may be electrically neutral (neutral ionophore) or charged (charged ionophore). Also ion-exchangers not capable of specific interactions with the target ion can be applied. It must be noted, that the presence of at least traces of ion exchanger is mandatory if an electrically neutral ionophore is used.

The membranes are typically based on a polymer such as polyvinyl chloride (PVC) or a polyurethane and usually also contain a water immiscible organic liquid which has plasticizer properties. However, none of the latter components is mandatory and both membranes without a polymer and polymer membranes without a plasticizer are known. Occasionally, some or all of the relevant components are covalently bonded to the polymer.

The present invention applies to all of the aforementioned types of ion-selective membrane electrodes. Other types of ion-selective electrodes are based on a sparingly soluble salt, such as silver halogenide or on glass (e.g., pH glass electrode). The present invention does not apply to these latter types of membranes.

In order to measure the potential; the membrane must be assembled into an electric circuit. One surface of the membrane contacts the sample solution while the other surface is electrically connected, via internal reference, to the potentiometric measurement equipment, which is further connected through a reference electrode to the sample solution. The internal reference may be a solid member, which directly contacts the ion-selective membrane. Examples of such a solid contact are platinum, platinum covered by a polypyrrole, graphite, or a chlorinated silver wire. On the other hand, the membrane can be directly deposited on a field effect transistor. So far, most commonly an electrolyte is applied at the inner membrane side, which is contacted to a reference electrode such as Ag/AgCl.

In spite of varying designs, the detection limit of practically all ion-selective solvent polymeric or liquid membrane electrodes is on the order of $10^{-6}$ M. For many applications, such as clinical analysis of a series of physiologically relevant ions, this if of no concern, but this detection limit prohibits the use of such electrodes for environmental monitoring of toxic heavy metal ions such as $Pb^{2+}$, $Cd^{2+}$, $Cu^{2+}$, $Ag^+$ and/or $Hg^{2+}$ because they should be detected at the submicromolar level. For example, the U.S. Environmental Protection Agency (EPA) (U.S. Environmental Protection Agency Office of Water and Hazardous Materials, *Quality Criteria for Water*, U.S. GPO; Washington, D.C., 1976) and the World Health Organization (World Health Organization, *Guidelines for Drinking Water Quality*, Vol. I; *Recommendations*; WHO; Geneva, 1984) tolerate a maximum amount of 0.05 mg of lead/L drinking water, which corresponds to a concentration of 2.4 $10^{-7}$ M $Pb^{2+}$. This level is below the detection limit of available ion-selective electrodes. The tolerated concentrations of other toxic ions of concern are at submicromolar concentrations as well. Another application, not feasible with the present technology is the analysis of physiologically relevant trace metal ions such as $Zn^{2+}$ in clinical samples.

In general, the detection limit of an ion-selective electrode can be caused by the presence of an interfering ion. However, detection limits around $10^{-6}$ M are also found in absence of such interferences. In such cases, there is no fundamental reason why the detection limit should not be much lower. Although the exact reason for the lack of much lower detection limits of such liquid membrane electrodes is not proven, it is believed that the primary ions leaching out of the membrane phase might be limiting. As a result, the local ion activity at the membrane surface (Nernstian boundary layer) is kept at a higher level independently of the concentration of the bulk sample.

This interpretation was suggested by the fact that lower detection limits below $10^{-6}$ M could be observed if the concentration of the measuring ions was buffered in the sample by using an ion buffer such as ethylenediamine tetraacetic acid (EDTA) or nitrillotriacetic acid. For example detection limits of $10^{-9}$ M have been reported for $Ca^{2+}$ (cf. Schefer, U.; Ammann, D.; Pretsch, E.; Oesch, U.; Simon, W. Neutral Carrier Based $Ca^{2+}$-Selective Electrode with Detection Limit in the Sub-Nanomolar Range. *Anal. Chim. Acta* 1986, 58, 2282–2285) and $Pb^{2+}$ (cf. Bakker, E.; Willer, M.; Pretsch, E. Detection limits of ion-selective bulk optodes and corresponding electrodes. *Anal. Chim. Acta* 1993, 282, 265–271) with such ion buffers. Such experiments are, however, only of academic interest because practically relevant samples do not contain any ion buffers.

Although these results make it likely that the higher than expected detection limits are caused by the ions leaching out of the membrane, the exact reason of this leaching process is not known. In the comprehensive standard reference volume on ion-selective electrodes Morf, W. E. *The Principles of Ion-Selective Electrodes and of Membrane Transport*, Elsevier; N.Y., 1981, various mechanisms are discussed for solid membrane electrodes (pp. 171–183) but the topic is not treated for solvent polymeric or liquid membrane electrodes. In the case of a $Pb^{2+}$ selective electrode, experiments were made with various concentrations of the inner reference electrolyte. It was however found that "The replacement of the inner filling electrolyte of the electrode by a solution buffered to $1.3 \times 10^{-7}$ M $Pb^{2+}$ did not significantly lower the detection limit" (cf. Bakker, E.; Willer, M.; Pretsch, E. Detection limits of ion-selective bulk optodes and corresponding electrodes. *Anal. Chim. Acta* 1993, 282, 265–271).

The idea that the interfering ions originate from the inner reference electrolyte is also disproved by the fact that no lower detection limits were reported with solid contact electrodes or with ion-selective field effect transistors which do not contain such an internal reference solution (see also Example 5). Thus according to present knowledge it was not expected that the detection limit of ion-selective electrodes would be influenced by the inner reference system.

SUMMARY OF THE INVENTION

A new type of ion-selective solvent polymeric or liquid membrane electrode has been constructed which enables the measuring range to be extended at the lower end by at least six (6) orders of magnitudes. The new method can be used with membranes based on a neutral ionophore, a charged ionophore, or an ion-exchanger.

Low detection limits are achieved by maintaining a very low and constant concentration of the primary ion and a sufficiently high concentration of an interfering ion in the internal reference solution. The low and constant concentration of the primary ion is either adjusted with the help of a solution of a hydrophilic ion buffer such as ethylenediamine tetraacetic acid or by adding an excess of a salt of an ion which forms a sparingly soluble salt with the primary ion, such as NaI for the primary ion $Ag^+$.

With this invention, ion-selective electrodes can be used, for the first time, for environmental monitoring of heavy metal ions such as $Pb^{2+}$ and $Cd^{2+}$ at the submicromolar level.

BRIEF DESCRIPTION OF THE DRAWINGS

In FIG. 7 the electrode has a conventional inner reference electrolyte and in FIG. 8 the same membrane is used with a solution of $10^{-3}$ M $CaCl_2$ and $10^{-1}$ M ethylenediamine tetraacetic acid tetrasodium salt as the inner reference electrolyte.

FIG. 9 shows the electrode response towards $AgNO_3$ when using a conventional inner reference electrolyte ($10^{-2}$ M $AgNO_3$). The detection limit in this case is $6 \times 10^{-8}$ M. In the second case, $10^{-15}$ M is achieved (FIG. 10).

DETAILED DESCRIPTION OF THE INVENTION

Figure 1:
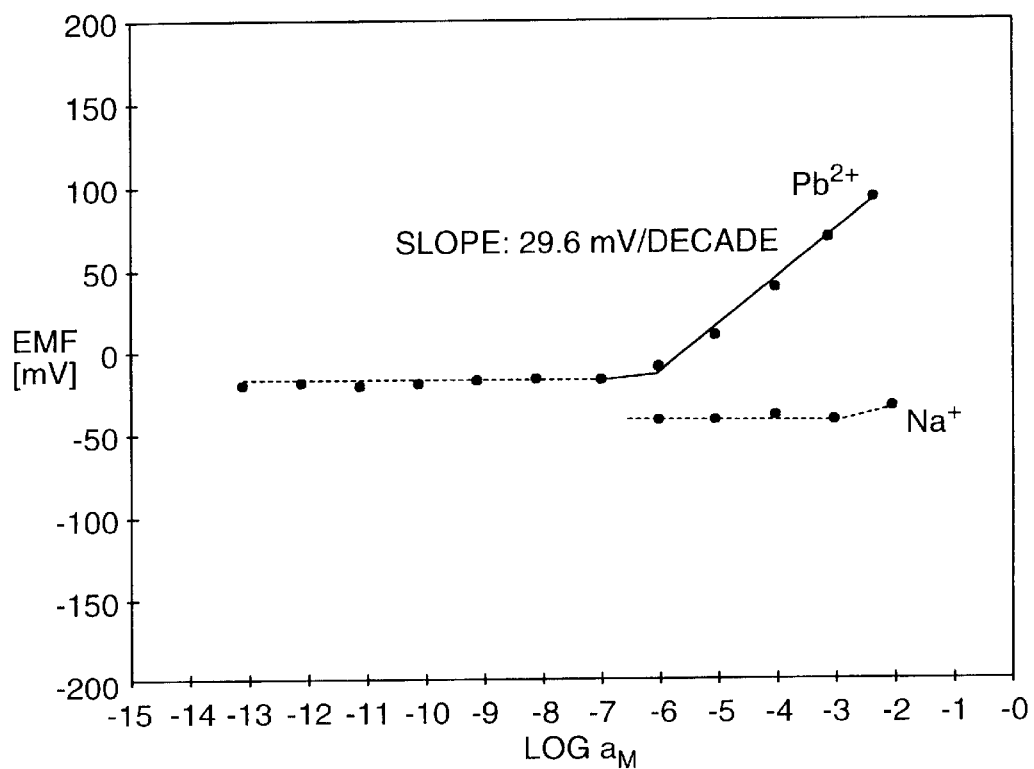
FIGS. 1 and 2 the compare the responses of two $Pb^{2+}$-ion-selective electrodes based on the ETH 5435 membrane.

As set forth above, one object of the present invention is the preparation of the ion-selective solvent polymeric or liquid membrane electrodes with low detection limits. This aspect of the invention was based on the surprising observation that the adjustment of the primary ion activity at the inner reference side of the membrane to a constant low level and a simultaneous maintaining of a higher concentration of an interfering ion massively decreases the lower detection limit. The measuring range of the electrodes confined to about 1 M to $10^{-6}$ M according to the prior art can be extended by at least six orders of magnitude so that a measuring range of 1 M to $10^{-12}$ M is now achieved. It is possible that even lower detection limits will be found by applying the new methods described herein. The present invention allows true trace material ion analysis and speciation at the submicromolar level, in fact down to picomolar concentrations.

Various ways of adjusting the primary ion activity in the reference electrolyte to a low and constant level are possible. According to one technique, a hydrophilic complexing agent is used in the inner filling solution. Ion buffers can be applied at a relatively high concentration so that the transport of traces of primary ions into the reference will not influence the ion activities in the inner electrolyte and will thus have no effect on the potential of the measurement circuit.

If necessary, the internal reference electrolyte can be separated from the internal reference electrode (e.g., Ag/AgCl) by a salt bridge or, alternatively, graphite can be used as internal reference electrode.

Another aspect of the present invention is that the required low and constant concentration of the primary ion is controlled by a sparingly soluble salt. According to this procedure, the inner reference solution contains an electrolyte, the one ion of which forms a sparingly soluble salt with the primary ion. For example, sodium iodide can be used as electrolyte in the case of a $Ag^+$-selective electrode. This second technique may be advantageous if the inner reference electrolyte is applied in a low volume i.e., with miniaturized ion-selective electrodes including field-effect transistor based systems.

Both of the above-described methods have in common that the primary ion is buffered in the reference compartment and has a high concentration (as a complex or as a precipitate) but a low activity (due to complex formation or to low solubility product).

Both techniques, i.e., an ion buffer or a counterion forming a sparingly soluble salt, can also be used without adding any primary ion to the internal electrolyte. As long as a sufficiently high concentration of an interfering ion is present in the inner electrolyte together with an agent keeping the activity of the primary ion leaching out of the membrane at a very low level, it is not necessary to add any primary ion to the reference electrolyte. It is also possible that $H^+$ acts as interfering ion so that no other has to be added to the internal electrolyte. In this case, solely the pH of the internal electrolyte must be buffered.

Improved measuring range can even be achieved by using the salt of an interfacing ion with or without that of the primary ion as inner electrolyte. The concentration of the interfering ion must be high enough to at least partly replace the primary ion at the inner membrane surface and thus generate a concentration gradient in the membrane. The necessary concentration of the interfering ion can be calculated with the improved Nicolskii-Eisenman equation (Selectivity of Polymer Membrane-Based Ion-Selective Electrodes: Self-Consistent Model Describing the Potentiometric Response in Mixed Ion Solutions of Different Charge. Bakker, E.; Meruva, R. K.; Pretsch, E.; Meyerhoff, M. E. *Anal. Chem.* 1994, 66, 3021–3030).

A further aspect of the present invention is the improvement of attainable selectivity factors. The usual procedures to measure selectivity factors are the separate solution method (SSM) and the fixed interference method (FIM) according to the recommendations of the International Union of Pure and Applied Chemistry (cf. Guilbault, G. G.; Durst, R. A.; Frant, M. S.; Freiser, H.; Hansen, E. H.; Light, T. S.; E. Pungor, Rechnitz, G.; Rice, N. M.; Rohm, T. J.; Simon, W.; Thomas, J. D. R. *Pure Appl. Chem.* 1976, 48, 127–132).

With SSM the potentials measured in pure solution of the primary and of the interfering ion are compared and with FIM the primary ion activity is varied at a fixed level of interfering ion activities. In both cases, the measured selectivities can be biased if an interfering ion is highly discriminated because the potential is not determined by such an ion but by the primary ions leaching out of the membrane (i.e., by the apparent lower detection limit of the electrode). Since the lower detection limit is reduced by the procedures described in this invention the selectivity coefficients obtained are also improved.

So far, true selectivity coefficients with respect of highly discriminated ions could only be measured by using a specific measurement protocol: The potential had to be measured for all discriminated ions before the electrode contacted the primary ion solution (cf. Bakker, E. Determination of unbiased selectivity coefficients of neutral carrier based cation-selective electrodes, *Anal. Chem.* 1997, 69, 1061–1069). However, this procedure involves an irreversible step: once the electrode is contacted with the preferred ions, the originally measured low potentials of the interfering ions cannot be reproduced any more. In contrast, the low potentials in the solutions of discriminated ions can be reversibly measured with the electrodes described herein.

Another method to assess true selectivity coefficients is based on the use of ion buffers in the sample solution (cf. Sokalski, T.; Maj-Zurawska, M.; Hulanicki, A. Determination of true selectivity coefficients of neutral carrier calcium selective electrode, *Mikrochim. Acta* 1991, 1, 285–291). This method is, however, limited to cases where a buffer is available which complexes the primary ion but not the interfering ion. Moreover, none of these methods can make use of the improved selectivity factors in a practical analytical application. In contrast, full use of the improved selectivities is made according to the present invention.

The present invention will be further illustrated with reference to the following examples which aid in the understanding of the present invention, but which are not to be construed as limitations thereof. All percentages reported herein, unless otherwise specified, are percent by weight. All temperatures are expressed in degrees Celsius.

EXAMPLE 1

Figure 2:
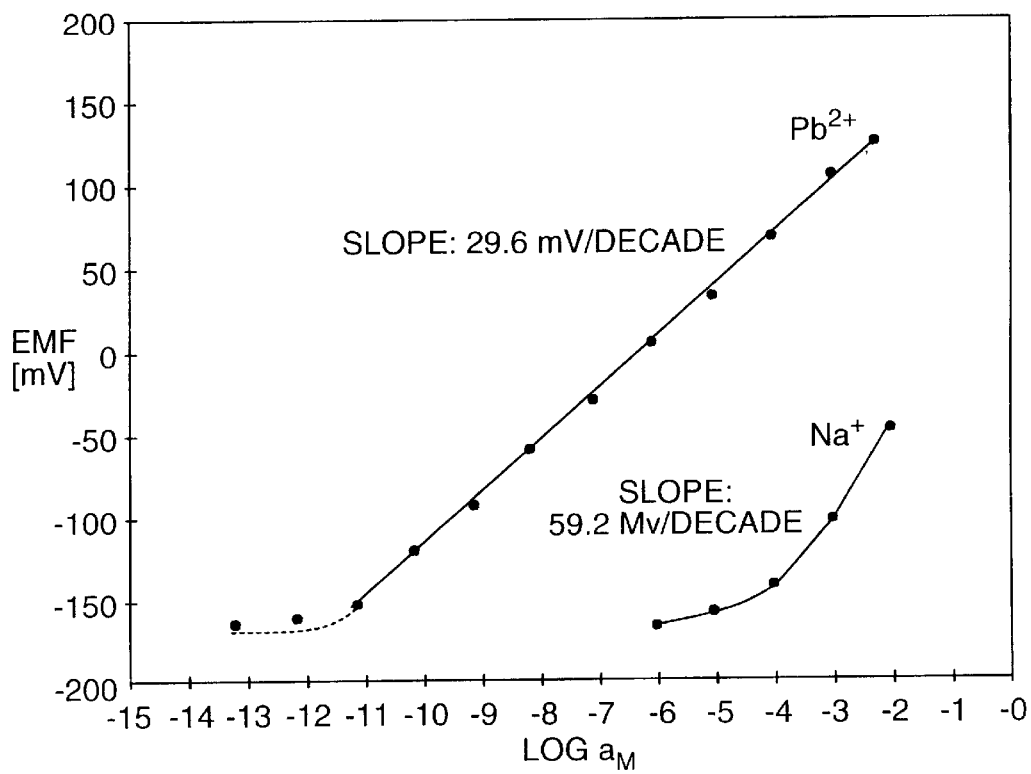

In FIGS. 1 and 2 the responses of two $Pb^{2+}$-ion-selective electrodes based on the same membrane are compared. The membrane composition in both electrodes is 14.9 mmol/kg N,N,N,N-tetradodecyl 3,6-dioxaoctanedioic acid dithioamide (ETH 5435), 9.1 mmol/kg potassium tetrakis [3,5-bis(trifluormethyl)phenyl] borate (KTFPB), 62.5 wt % bis(2-ethylhexyl) sebacate (DOS), and 35.3 wt % poly(vinyl chloride) (PVC).

In the first case (FIG. 1), a conventional inner reference electrolyte was used (composition: $5 \times 10^{-4}$ M $PbCl_2$, $5 \times 10^{-2}$ M $MgCl_2$). The lower detection limit is $4 \times 10^{-6}$ M in this case. Measurements with a membrane of the same composition are shown in FIG. 2 where the composition of the inner reference electrolyte was $10^{-3}$ M $Pb(NO_3)_2$ and $5 \times 10^{-2}$ M ethylenediamine tetraacetic acid disodium salt (EDTA-$Na_2$) as an ion buffer. The inner reference electrode (Ag/AgCl) was separated from the EDTA solution by a 1 M KCl salt bridge. The linear Nernstian response range is extended to about $10^{-11}$ M and the lower detection limit to $5 \times 10^{-12}$ M. Also the difference of the response towards $Na^+$ is striking. The potential does not depend on the activity of $Na^+$ in FIG. 1, since here it is not the potential determining ion. On the contrary, Nernstian response is observed also for $Na^+$ down to a concentration of $10^{-3}$ M.

EXAMPLE 2

By using the two electrodes as described in Example 1 without and with an ion buffer in the inner reference solution (FIGS. 1 and 2) selectivity factors were determined by the separate solution method (Table 1). Apparently an improvement of the selectivity coefficients with respect of all strongly discriminated ions is found with the new technique. As expected, especially large differences are observed with the highly discriminated ions, such as $Na^+$, $K^+$, $Mg^{2+}$, and $Ca^{2+}$ for which the insufficient detection limit of a conventional $Pb^{2+}$ electrode biased the results.

Table 1 is presented below. As shown therein, potentiometric logarithmic selectivity factors, log $K(^{Po}:/PbM)$, determined by the separate solution method with the ion selective membrane described in Example 1 without (cf. FIG. 1) and with (cf. FIG. 2) an ion buffer in the internal reference electrolyte. The pH of the sample solution was adjusted to 4.1 with a $10^{-3}$ M Mg acetate buffer.

TABLE I

| Ion M | Traditional Electrode | New Inner Reference |
|---|---|---|
| H+ | −2.2 | −3.5 |
| Li+ | −2.7 | −5.1 |
| Na+ | −2.2 | −4.7 |
| K+ | −2.2 | −4.1 |
| $NH_4$+ | −2.5 | −4.1 |
| $Mg^2$+ | −3.6 | −9.4 |
| $Ca^2$+ | −4.0 | −8.6 |
| $Sr^2$+ | −4.2 | −6.7 |
| $Ba^2$+ | −4.1 | −6.0 |
| $Mo^2$+ | −4.1 | −5.8 |
| $Co^2$+ | −4.3 | −6.3 |
| $Ni^2$+ | −4.2 | −5.9 |
| $Cu^2$+ | −0.5 | −0.4 |
| $Zn^2$+ | −3.7 | −5.0 |
| $Cd^2$+ | 0.9 | 0.4 |

EXAMPLE 3

Figure 3:
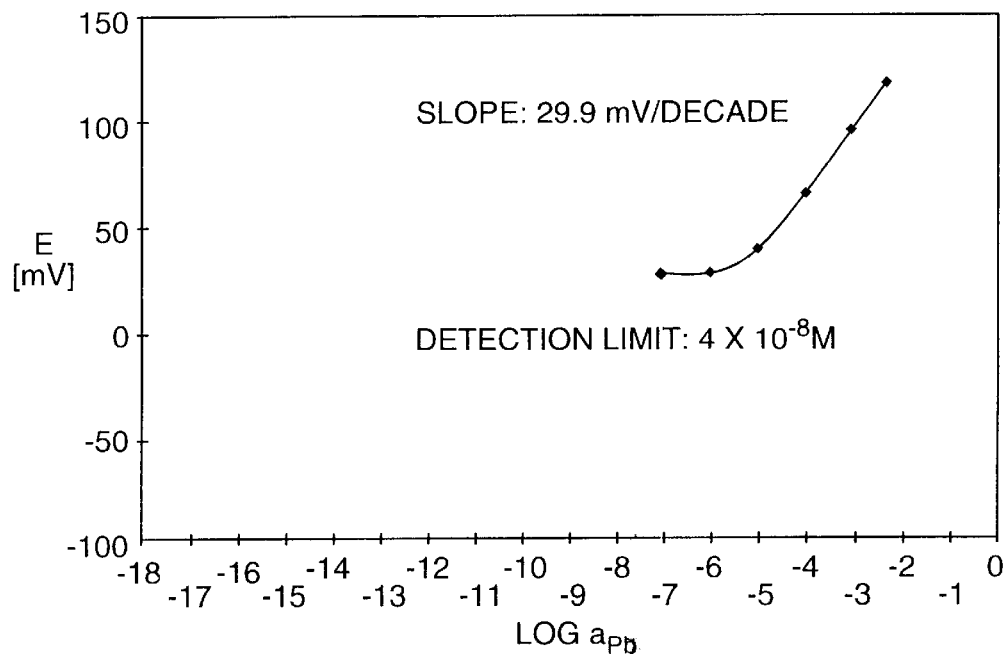
FIGS. 3 and 4 compare the responses of two $Pb^{2+}$-ion-selective electrodes based on the ETH 5493 membrane.
Figure 4:
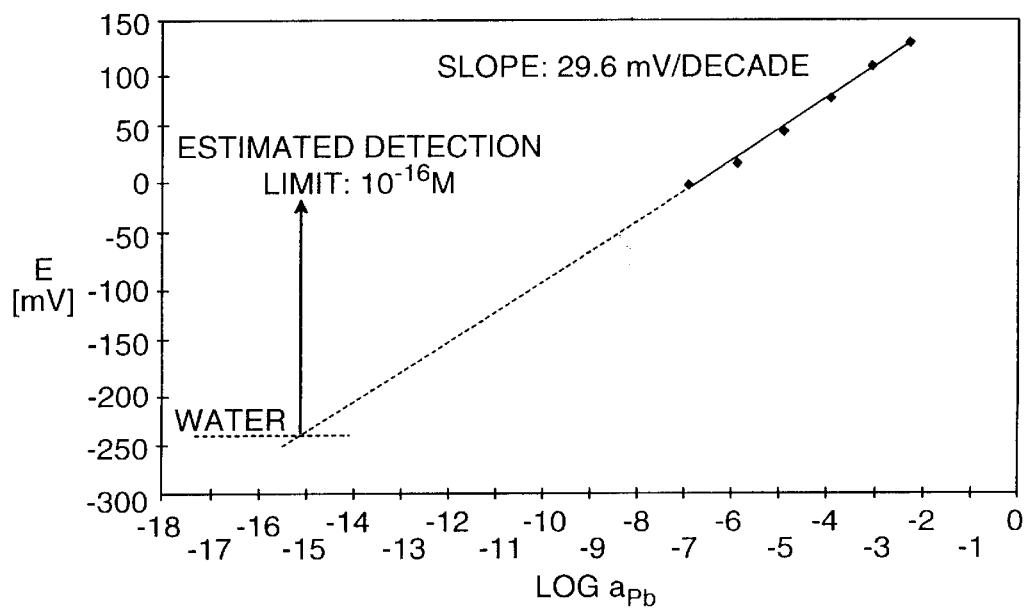

The response of two $Pb^{2+}$ ion selective electrodes based on the same membrane are compared in FIGS. 3 and 4. In this case N,N,N,N-tetradodecyl 3,6-dioxaoctanedioic acid monothioamide (ETH 5493) was used as the $Pb^{2+}$-selective ionophore instead of ETH 5435 (Examples 1 and 2). The membrane composition used in both cases was: 16 mmol/kg ETH 5493, 10 mmol/kg potassium tetrakis[3,5-bis(trifluormethyl)phenyl] borate (KTFPB), 35 wt % poly(vinyl chloride) (PVC).

In the first case (FIG. 3), by using a conventional inner reference electrolyte (composition: $10^{-4}$ M $PbCl_2$, 0.01 M $MgCl_2$, 0.01 M Mg-acetate buffer, pH=4.6) was used a lower detection limit of $4 \times 10^{-6}$ M was found. Measurements with a membrane of the same composition are shown in FIG. 4 where the inner reference electrolyte was $10^{-3}$ M $Pb(NO_3)_2$ and $5 \times 10^{-2}$ M ethylenediamine tetraacetic acid disodium salt (EDTA$Na_2$). A lower detection limit of $10^{-15}$ M is estimated from the response slope and the potential measured in pure water. The inner reference electrode (Ag/AgCl) was separated from the EDTA solution by a salt bridge of 1 M KCl.

EXAMPLE 4

Figure 5:
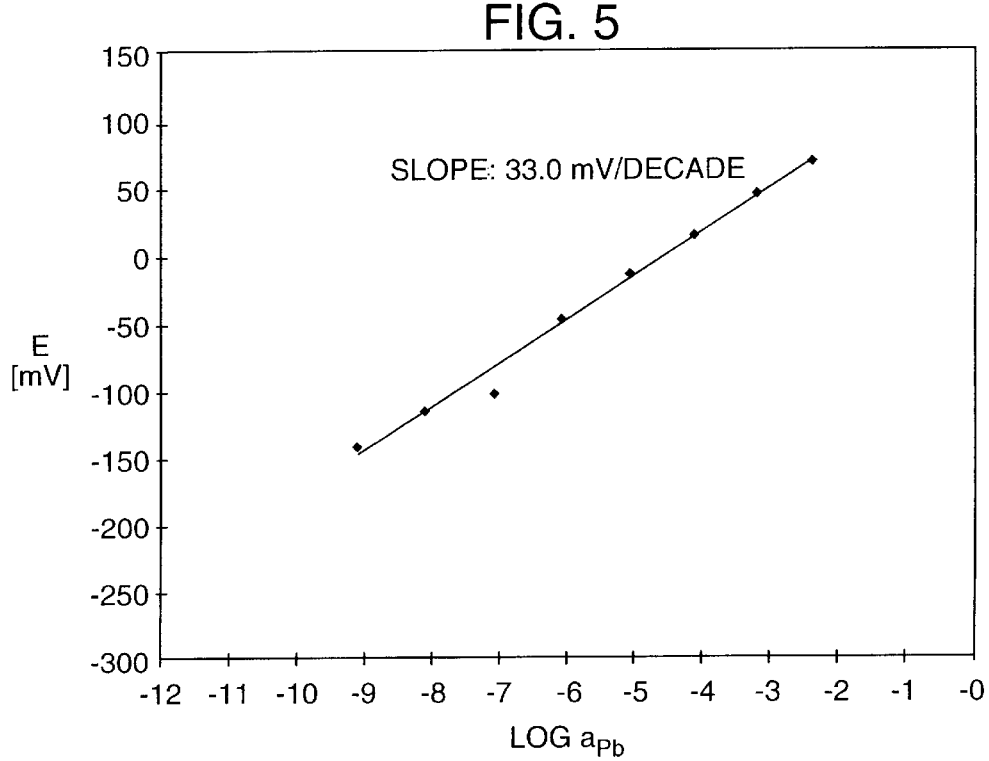
FIG. 5 shows the response of an electrode using the same membrane composition as used as in FIG. 4 to various $PbCl_2$ solutions. In this case the inner reference electrode was graphite.

In this example the same membrane and buffered inner filling solution was used as in the previous Example (FIG. 4). The only difference is that instead of a bridge electrolyte and Ag/AgCl, a graphite rod was used as an inner reference electrode. Since no interaction with the inner reference electrolyte ($5 \times 10^{-2}$ M ethylenediamine tetraacetic acid disodium salt, EDTA-Na$_2$) is expected, there is no need for a salt bridge. As shown in FIG. 5, the response of this electrode to various PbCl$_2$ solutions is linear down to at least $10^{-9}$ M.

EXAMPLE 5

Figure 6:
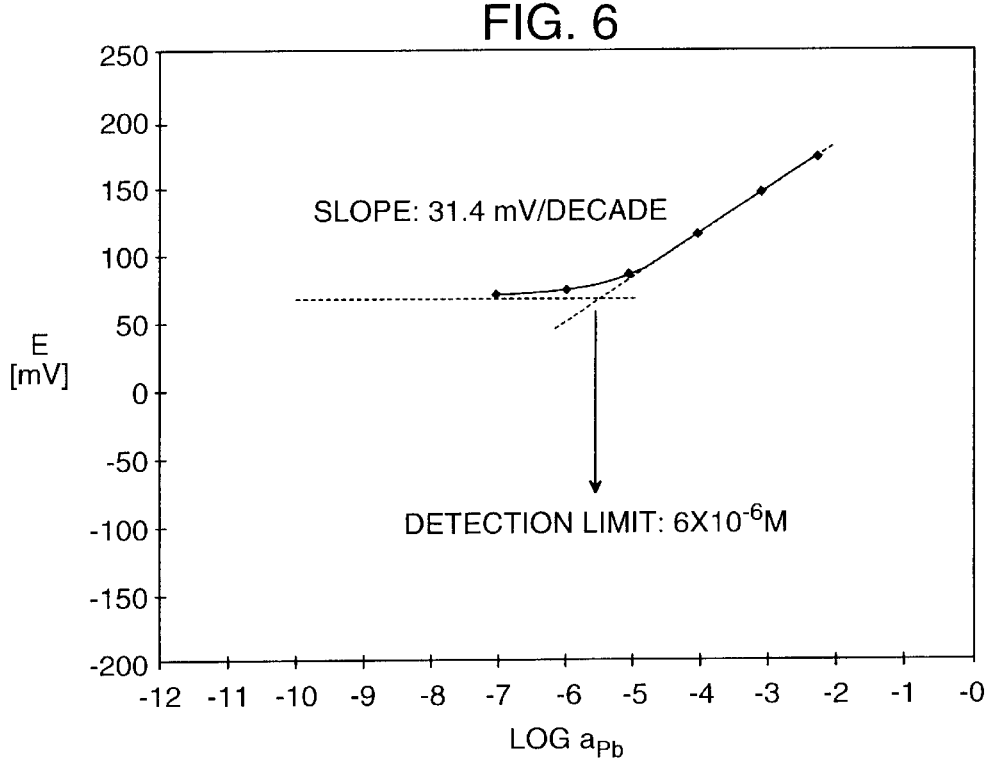
FIG. 6 shows the response of an electrode using the same membrane composition as used as in FIGS. 3 and 4 to various $PbCl_2$ solutions. In this case the inner reference electrode was graphite but no inner reference electrolyte was used.

In this example again the same membrane composition was used as in Examples 3 and 4. The inner reference electrode was graphite but no inner reference electrolyte was used. Instead, the membrane directly contacted the graphite surface, i.e.; graphite was used as a solid contact inner reference electrode. The response of this electrode to various PbCl$_2$ solutions is shown in FIG. 6. The lower detection limit here is $6 \times 10^{-6}$ M and thus the same as with a conventional electrode (FIG. 3). This example proves the decisive importance of the special inner reference electrolyte which maintains a low and constant concentration of Pb$^{2+}$ at the reference side of the ion-selective membrane.

EXAMPLE 6

Figure 7:
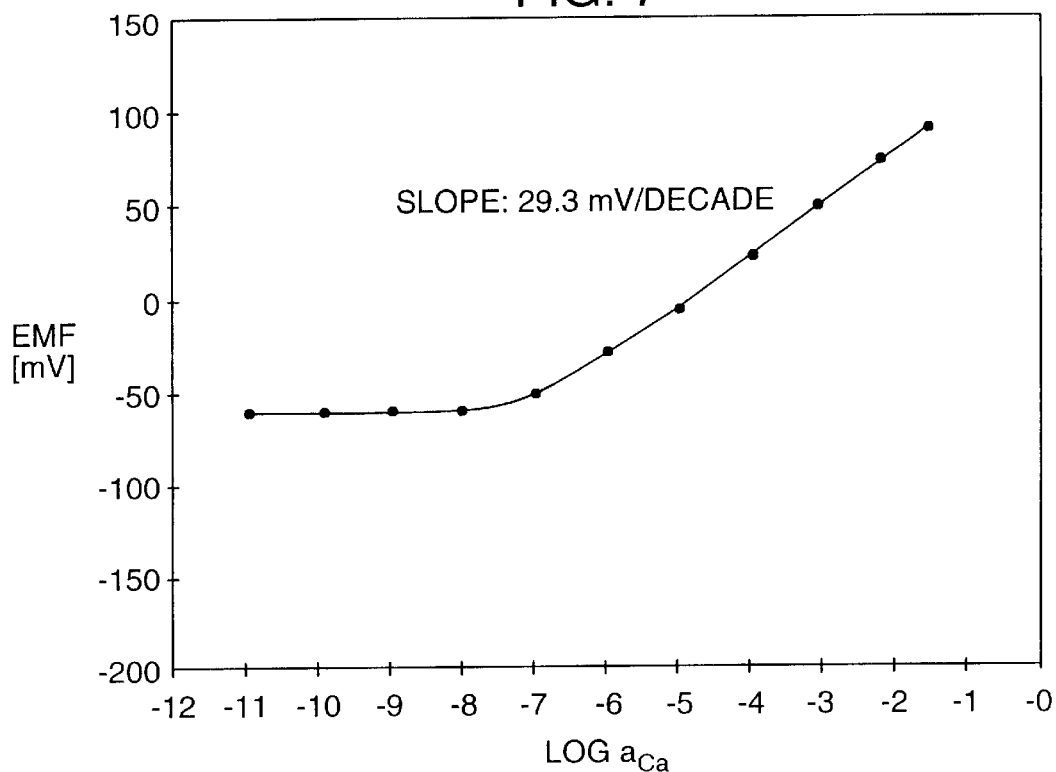
FIGS. 7 and 8 compare the responses of two $Pb^{2+}$-ion-selective electrodes based on the ETH 5234 membrane.
Figure 8:
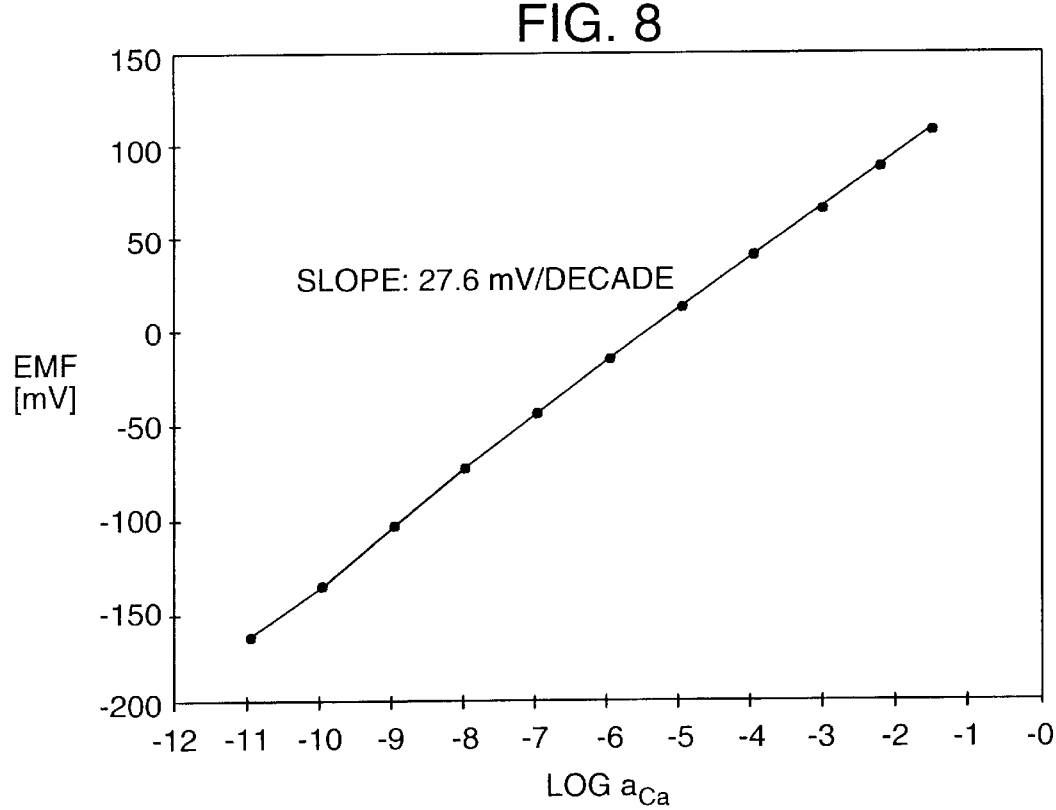

In this example the method is applied to a Ca$^{2+}$ selective membrane based on the ionophore N,N-dicyclohexyl-N,N-dioctadecyl-3oxapentanamide (ETH 5234). In FIG. 7 the electrode response is shown for a conventional inner reference electrolyte and in FIG. 8 the same membrane is used with a solution of $10^{-3}$ M CaCl$_2$ and $10^{-1}$ M ethylenediamine tetraacetic acid tetrasodium salt (EDTA-Na$_4$) as inner reference electrolyte. The membrane composition is in both cases: 12.8 mmol/kg ETH 5234. 3.2 mmol/kg potassium tetrakis[3,5-bis(trifluormethyl)phenyl] borate (KTFPB), 63.7 wt % bis(2-ethylhexyl) sebacate (DOS), and 35.0 wt % poly(vinyl chloride) (PVC). The linear response range down to about $10^{-6}$ M CaCl$_2$ of the conventional electrode (FIG. 7) was extended to $\geq 10^{-11}$ M with the novel inner electrolyte.

This example demonstrates the general applicability of the technique described in this invention by showing that it is not limited to Pb$^{2+}$ shown in the Examples 1–5.

EXAMPLE 7

Figure 9:
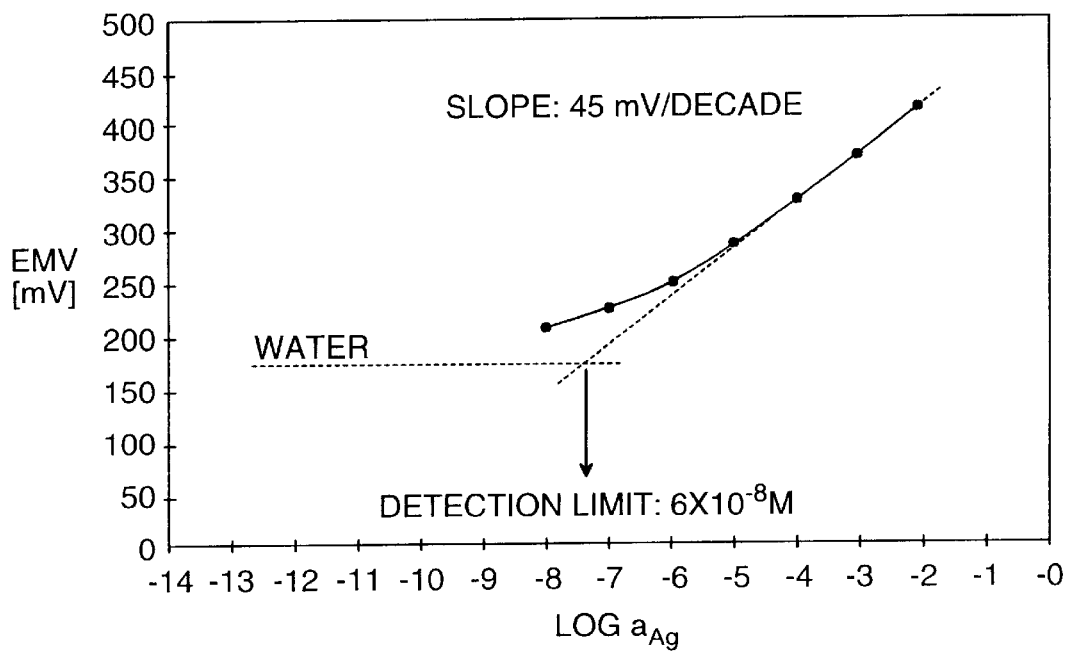
FIGS. 9 and 10 compare the responses of two $Pb^{2+}$-ion-selective electrodes based on the use of a sparingly soluble salt to buffer the primary ion at a low activity level.
Figure 10:
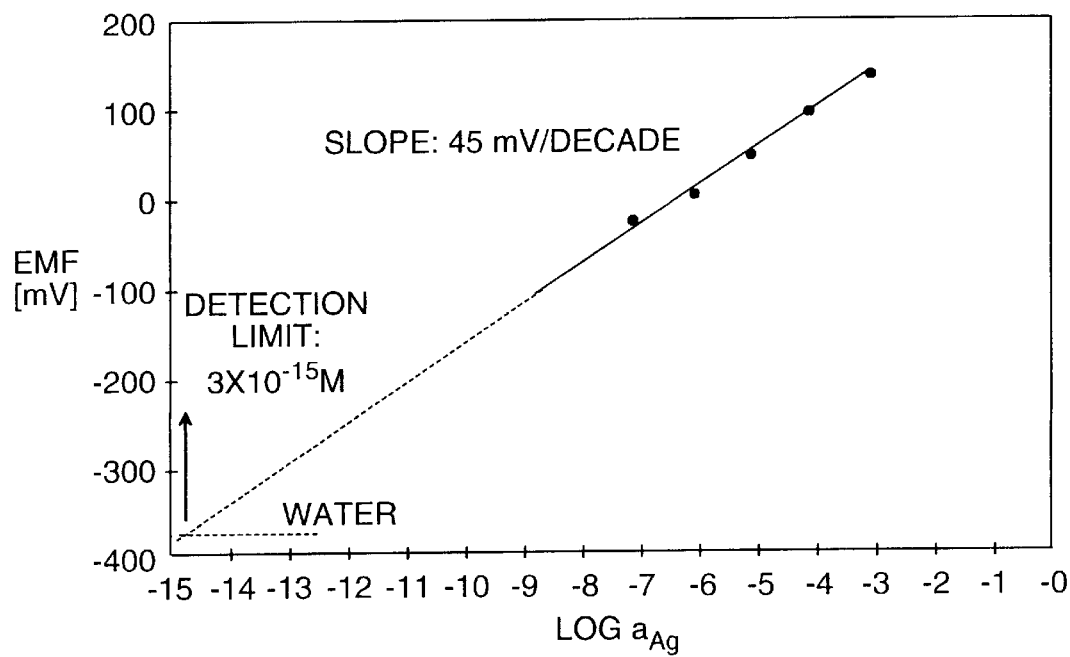

This example shows the application of a sparingly soluble salt to buffer the primary ion at a low activity level ion buffering. An Ag$^+$-selective membrane of the following composition was used: 12.8 mmol/kg S,S-methylene-bis (diisobutyldithiocarbamate), 3.6 mmol/kg potassium tetrakis[3,5-bis(trifluormethyl)phenyl] borate (KTFPB), 67.2 wt % bis(2-ethylhexyl) sebacate (DOS), and 32.1 wt % poly(vinyl chloride) (PVC). FIG. 9 shows the electrode response towards AgNO$_3$ when using a conventional inner reference electrolyte ($10^{-2}$ M AgNO$_3$). The detection limit in this case is $6 \times 10^{-8}$ M. In the second case, $10^{-15}$ M is achieved (FIG. 10).

This not only shows that the use of a sparingly soluble salt in the inner reference electrolyte to maintain the required low and constant activity of the primary ion leads to the same result as ion buffering but also that no addition of any primary ion to the inner electrolyte is necessary. Furthermore, it illustrates that the method is not just limited to Pb$^{2+}$- and Ca$^{2+}$-ion-selective electrodes. Since for most ions of interest either ion buffers or selectivity hydrophilic complexing agents can be found, the invention has a very general applicability.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. An ion selective electrode comprising an ionophore selected from the group consisting of a neutral ionophore, a charged ionophore, and an ion exchanger in which the ion selective electrode has an inner reference electrolyte containing a well defined low and constant activity of the primary ion that is directly contacted to graphite as an inner reference electrode.

2. A method of monitoring ions below activities of $10^{-6}$M said method comprising the steps of:

contacting a test solution containing such ions with an electrode as defined in any of claims 1, 7, 8, 9 and measuring the activity of such ions therewith.

3. The method of claim 2, wherein the ions monitored are ions of environmental concern selected from the group consisting of Pb$^{2+}$, Cd$^{2+}$, Cu$^{2+}$, Cu$^{2+}$, Ag$^+$, and Hg$^{2+}$.

4. The method of claim 2, wherein the ions monitored are biologically relevant trace metal ions in body fluids.

5. The method of claim 4, wherein the biologically relevant trace metal ion being monitored is Zn$^{2+}$.

6. The method of claim 4, wherein the biologically relevant trace metal ion being monitored is Cu$^{2+}$.

7. A cation or anion selective ion-selective membrane electrode, said membrane electrode based on an ionophore selected from the group consisting of a neutral ionophore, a charged ionophore, and an ion exchanger, wherein the membrane has an inner side and an outer side, the inner side of said membrane contacting a reference electrolyte, said electrolyte comprising an interfering ion of sufficiently high activity and a primary ion of sufficiently low activity, the relative magnitudes of said activities being calculable from the modified Nernst-Nicolsky equation, such that the interfering ion at least partly replaces the primary ion in the membrane, thereby generating a concentration gradient across the membrane, said electrolyte further comprising an agent that serves to maintain the primary ion at said sufficiently low activity despite any flux of primary ion through the membrane from the sample under the influence of said concentration gradient.

8. An electrode as defined in claim 7, wherein the agent that maintains the low activity of the primary ion comprises a hydrophilic ion-buffer selected from the group consisting of ethylendiamine tetraacetic acid, nitrilotriacetic acid, a cation complexing agent and an anion complexing agent.

9. An electrode as defined in claim 7, wherein the agent that maintains the low activity of the primary ion comprises a counterion of the primary ion which forms a sparingly soluble salt with the primary ion.

10. An electrode as defined in any of claims 7 to 9, wherein no primary ion is added to the internal electrolyte.

11. An electrode as defined in claim 7, wherein the inner reference electrolyte further comprises a hydrophilic ion buffer to maintain a constant low activity of the primary ion.

* * * * *